United States Patent [19]

Wroblowsky et al.

[11] Patent Number: 4,874,420
[45] Date of Patent: Oct. 17, 1989

[54] HERBICIDAL SUBSTITUTED TRIAZINES

[75] Inventors: Heinz-Jürgen Wroblowsky; Joachim Kluth; Klaus-Günther Tietjen, all of Langenfeld; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 220,036

[22] Filed: Jul. 15, 1988

[30] Foreign Application Priority Data

Jul. 23, 1987 [DE] Fed. Rep. of Germany ....... 3724378
Jan. 16, 1988 [DE] Fed. Rep. of Germany ....... 3801113

[51] Int. Cl.$^4$ .................. A01N 43/70; C07D 251/50; C07D 251/52; C07D 251/18
[52] U.S. Cl. ........................................ 71/93; 544/208; 544/209; 544/206; 544/207; 544/205; 544/204; 544/210
[58] Field of Search .................... 71/93; 544/208, 209, 544/206, 207, 205, 204, 210

[56] References Cited

PUBLICATIONS

Chemie der Pflanzenschutz- und Schädlings- bekämpfungsmittel, vol. 5, Herbizide, R. Wegler, Springer-Verlag, Berlin, 1977, pp. 336–352.

*Primary Examiner*—John M. Ford
*Attorney, Agent, or Firm*—Sprung Horn Kramer & Woods

[57] ABSTRACT

Herbicidal substituted triazines of the formula

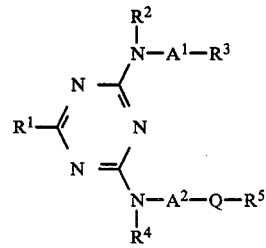

in which
$A^1$ represents optionally branched and optionally aryl-substituted alkanediyl,
$A^2$ represents optionally branched alkanediyl,
Q represents oxygen, sulphur, NH or N-alkyl,
$R^1$ represents hydrogen, hydroxyl, nitro, cyano, cyanoamino, azido, halogen, alkoxy, alkylthio (which is optionally substituted by halogen or cyano), alkyl, alkoxycarbonyl, aminocarbonyl, alkylaminocarbonyl, dialkylaminocarbonyl, amino, alkylamino or dialkylamino,
$R^2$ represents hydrogen, alkyl, alkenyl or alkinyl,
$R^3$ represents optionally substituted aryl or heteroaryl,
$R^4$ represents hydrogen, alkyl, alkenyl or alkinyl and
$R^5$ represents hydrogen or alkyl.

8 Claims, No Drawings

HERBICIDAL SUBSTITUTED TRIAZINES

The invention relates to new substituted triazines, processes for their preparation and their use as herbicides.

It is known that certain substituted triazines, such as, for example, 2-chloro-4-ethylamino-6-isopropylamino-s-triazine (atrazine) can be used as herbicides compare "Chemie der Pflanzenschutz- und Schädlingsbekämpfungsmittel" ("Chemistry of Plant Protection Agents and Agents for Combating Pests"), Volume 5—"Herbizide" (Herbicides), published by R. Wegler, Springer-Verlag, Berlin, Heidelberg, New York 1977, pages 336–352). However, the action of the compound mentioned against miliary weeds, such as, for example, Digitaria and Panicum, is not always completely satisfactory.

New substituted triazines of the general formula (I)

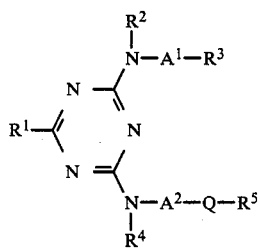
(I)

in which
  $A^1$ represents optionally branched and optionally aryl-substituted alkanediyl ("alkylene"),
  $A^2$ represents optionally branched alkanediyl "(alkylene"),
  Q represents oxygen, sulphur, NH or N-alkyl,
  $R^1$ represents hydrogen, hydroxyl, nitro, cyano, yanoamino, azido, halogen, alkoxy, alkylthio (which is optionally substituted by halogen or cyano), alkyl, alkoxycarbonyl, aminocarbonyl, alkylaminocarbonyl, dialkylamino-carbonyl, amino, alkylamino or dialkylamino,
  $R^2$ represents hydrogen, alkyl, alkenyl or alkinyl,
  $R^3$ represents optionally substituted aryl or heteroaryl,
  $R^4$ represents hydrogen, alkyl, alkenyl or alkinyl and
  $R^5$ represents hydrogen or alkyl,
have now been found.

It has furthermore been found that the new substituted triazines of the general formula (I) are obtained by a process in which
  (a) halogenated triazines of the general formula (II)

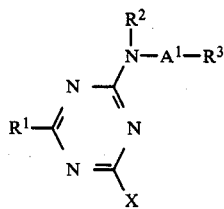
(II)

in which
  $A^1$, $R^1$, $R^2$ and $R^3$ have the abovementioned meanings and
  X represents halogen, are reacted with amino compounds of the general formula (III)

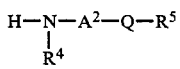
(III)

in which
  $A^2$, Q, $R^4$ and $R^5$ have the abovementioned meanings,
if appropriate in the presence of an acid acceptor and if appropriate in the presence of a diluent, or
  (b) halogenated triazines of the general formula (IV)

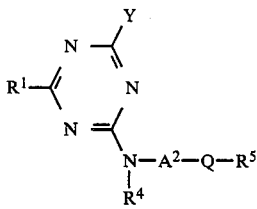
(IV)

in which
  $A^2$, Q, $R^1$, $R^4$ and $R^5$ have the abovementioned meanings and
  Y represents halogen,
are reacted with amino compounds of the general formula (V)

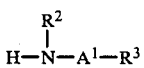
(V)

in which
  $A^1$, $R^2$ and $R^3$ have the abovementioned meanings,
if appropriate in the presence of an acid acceptor and if appropriate in the presence of a diluent, or
in the case where $R^1$ represents amino, alkylamino, dialkylamino, alkoxy or alkylthio
  (c) halogenated triazines of the general formula (VI)

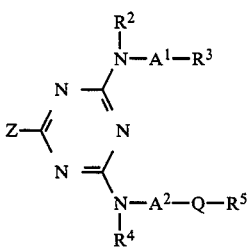
(VI)

in which
  $A^1$, $A^2$, Q, $R^2$, $R^3$, $R^4$ and $R^5$ have the abovementioned meanings and
  Z represents halogen,
are reacted with ammonia, alkylamines, dialkylamines, alkanols or alkanethiols or with alkali metal salts thereof, if appropriate in the presence of an acid acceptor and if appropriate in the presence of a diluent, or
in the case where $R^1$ represents alkylthio (which is optionally substituted by halogen or cyano)
  (d) mercaptotriazines of the general formula (VII)

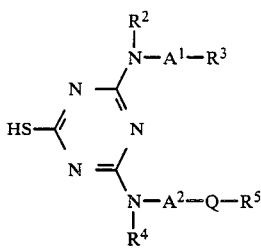

(VII)

in which

A$^1$, A$^2$, Q, R$^2$, R$^3$, R$^4$ and R$^5$ have the above-mentioned meanings, are reacted with halogen compounds of the general formula (VIII)

$$Z^1-R^6 \qquad (VIII)$$

in which

R$^6$ represents alkyl (which is optionally substituted by halogen or cyano) and Z$^1$ represents halogen, if appropriate in the presence of an acid acceptor and if appropriate in the presence of a diluent.

The new substituted triazines of the general formula (I) are distinguished by a powerful herbicidal activity.

Surprisingly, the compounds of the general formula (I) according to the invention exhibit a better selectivity in crop plants and a considerably more powerful action against weeds than known compounds of comparable structure and action profile.

The invention preferably relates to compounds of the formula (I) in which

A$^1$ represents optionally branched and optionally phenyl-substituted alkanediyl ("alkylene") with 1 to 4 carbon atoms, A$^2$ represents optionally branched alkanediyl ("alkylene") with 1 to 4 carbon atoms, Q represents oxygen, sulphur, NH or N-(C$_1$-C$_4$-alkyl), R$^1$ represents hydrogen, hydroxyl, nitro, cyano, cyanoamino, azido, fluorine, chlorine, bromine, iodine, C$_1$-C$_4$-alkoxy, C$_1$-C$_4$-alkylthio (which is optionally substituted by cyano, fluorine and/or chlorine), C$_1$-C$_4$-alkyl, C$_1$-C$_4$-alkoxy-carbonyl, aminocarbonyl, C$_1$-C$_4$-alkyl-amino-carbonyl, di-(C$_1$-C$_4$-alkyl)-amino-carbonyl, amino, C$_1$-C$_4$-alkylamino or di-(C$_1$-C$_4$-alkyl)-amino, R$^2$ represents hydrogen, C$_1$-C$_4$-alkyl, C$_2$-C$_4$-alkenyl or C$_2$-C$_4$-alkinyl, R$^3$ represents an aromatic or heteroaromatic grouping from the series comprising phenyl, naphthyl, pyridyl, quinolinyl, isoquinolinyl, pyrimidinyl, furyl, thienyl, pyrrolyl, pyrazolyl and imidazolyl which is optionally substituted by fluorine, chlorine, bromine, iodine, cyano, nitro, C$_1$-C$_4$-alkyl (which is optionally substituted by fluorine and/or chlorine), C$_1$-C$_4$-alkoxy or C$_1$-C$_2$-alkylenedioxy (which is optionally substituted by fluorine and/or chlorine), C$_1$-C$_4$-alkylthio, C$_1$-C$_4$-alkyl-sulphinyl or C$_1$-C$_4$-alkylsulphonyl (which are optionally substituted by fluorine and/or chlorine), di-(C$_1$-C$_2$-alkyl)-amino and/or by C$_1$-C$_4$-alkoxy-carbonyl, R$^4$ represents hydrogen, C$_1$-C$_4$-alkyl, C$_2$-C$_4$-alkenyl or C$_2$-C$_4$-alkinyl and R$^5$ represents hydrogen or C$_1$-C$_4$-alkyl.

The invention particularly relates to compounds of the formula (I) in which

A$^1$ represents optionally branched and optionally phenyl-substituted alkanediyl ("alkylene") with 1 to 3 carbon atoms, A$^2$ represents optionally branched alkanediyl ("alkylene") with 1 to 3 carbon atoms, Q represents oxygen, sulphur, NH or N—CH$_3$, R$^1$ represents cyanoamino, azido, fluorine, chlorine, bromine, methoxy, ethoxy, methylthio, ethylthio, difluoromethylthio, cyanomethylthio, methyl, amino, methylamino or dimethylamino, R$^2$ represents hydrogen or methyl, R$^3$ represents phenyl or naphthyl which are optionally substituted by fluorine, chlorine, bromine, cyano, nitro, methyl, ethyl, methoxy and/or ethoxy, or represents pyridyl which is optionally substituted by fluorine, chlorine, bromine, cyano, nitro, methyl, ethyl, methoxy and/or ethoxy, or represents furyl which is optionally substituted by fluorine, chlorine, bromine, methyl and/or ethyl, R$^4$ represents hydrogen or methyl and R$^5$ represents C$_1$-C$_3$-alkyl.

Especially preferred compounds of the formula (I) are those in which

A$^1$ represents ethane-1,1-diyl ("ethylidene"), the groupings bonded to the C atom in the 1-position of the ethane-1,1-diyl being arranged in an S-configuration, A$^2$ represents ethane-1,2-diyl ("ethylene") or propane-1,3-diyl ("trimethylene"), Q represents oxygen, R$^1$ represents chlorine, methoxy or methylthio, R$^2$ represents hydrogen, R$^3$ represents phenyl, R$^4$ represents hydrogen and R$^5$ represents methyl or ethyl.

If, for example, 2,4-dichloro-6-benzylamino-s-triazine and 3-methoxy-propylamine are used as starting substances, the course of the reaction in process (a) according to the invention can be outlined by the following equation:

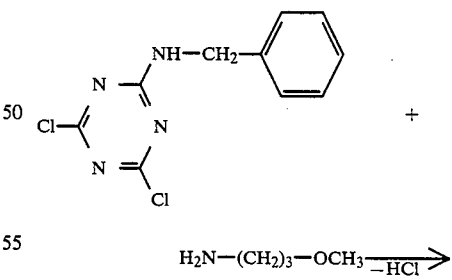

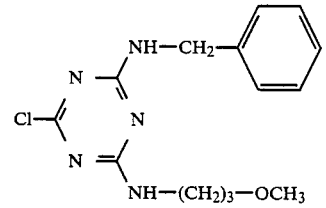

If, for example, 2-chloro-4-methoxy-6-(2-ethoxyethylamino)-s-triazine and 2-phenylethylamine are used as starting substances, the course of the reaction in process (b) according to the invention can be outlined by the following equation:

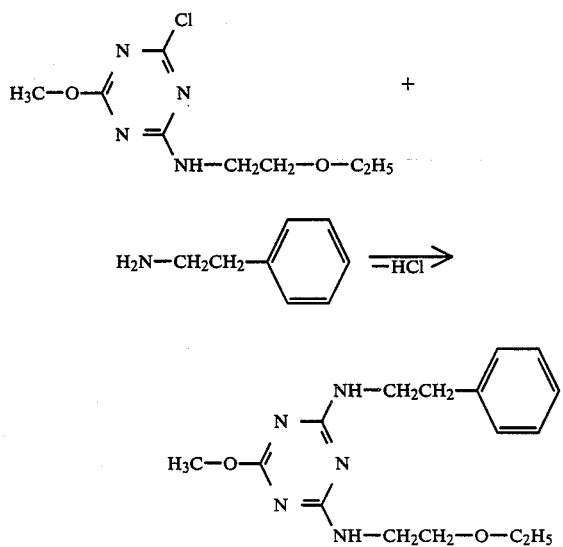

If, for example, 2-chloro-4-(2-methoxy-ethylamino)-6-(2-chloro-pyridin-5-yl-methylamino)-s-triazine and sodium methanethiolate are used as starting substances, the course of the reaction in process (c) according to the invention can be outlined by the following equation:

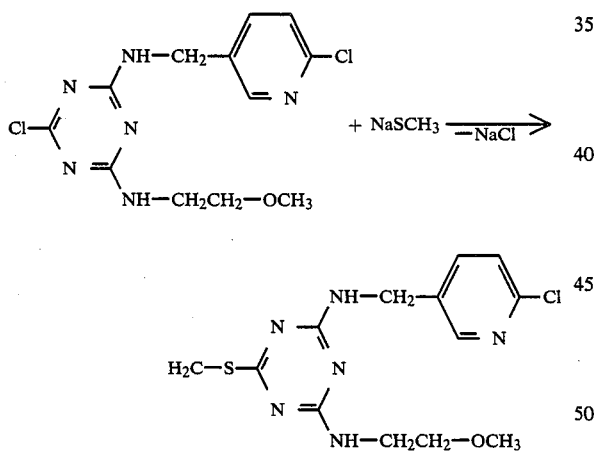

If, for example, 2-mercapto-4-(2-methoxyethylamino)-6-(2-phenyl-ethylamino)-s-triazine and chloroacetonitrile are used as starting substances, the course of the reaction in process (d) according to the invention can be outlined by the following equation:

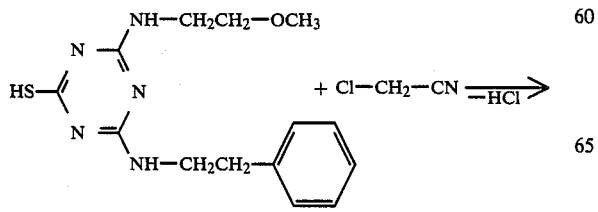

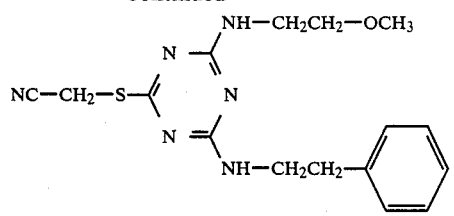

Formula (II) provides a general definition of the halogenated triazines to be used as starting substances in process (a) according to the invention. In formula (II), $A^1$, $R^1$, $R^2$ and $R^3$ preferably or particularly or especially preferably have those meanings which have already been mentioned above as preferred or as particularly preferred or as especially preferred for $A^1$, $R^1$, $R^2$ and $R^3$ in the context of the description of the compounds of the formula (I) according to the invention, and X preferably represents fluorine, chlorine or bromine, in particular chlorine.

Examples of the starting substances of the formula (II) are listed in the following Table 1.

TABLE 1

Examples of the starting substances of the formula (II)

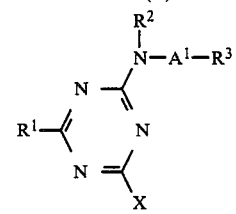

| $A^1$ | $R^1$ | $R^2$ | $R^3$ | X |
|---|---|---|---|---|
| $CH_2$ | Cl | H | 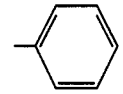 | Cl |
| $CHCH_3$ | Cl | H | 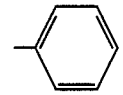 | Cl |
| $CH_2$ | Cl | $CH_3$ | 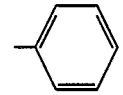 | Cl |
| $CH_2$ | Cl | H | 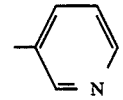 | Cl |
| $CH_2$ | Cl | H | 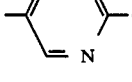 | Cl |
| $CHCH_3$ | Cl | $CH_3$ | 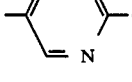 | Cl |

TABLE 1-continued

Examples of the starting substances of formula (II)

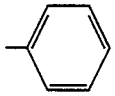

| A¹ | R¹ | R² | R³ | X |
|---|---|---|---|---|
| CHCH₃ | OCH₃ | H | 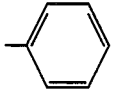 | Cl |
| CHCH₃ | SCH₃ | H |  | Cl |
| CHCH₃ | Cl | H | 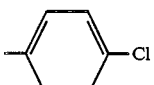 (–F) | Cl |
| CHCH₃ | Cl | H | 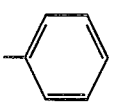 (–Cl) | Cl |
| CH₂CH₂ | Cl | H |  | Cl |
| CH₂ | Cl | H | 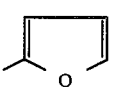 (furan) | Cl |
| CH₂ | Cl | H | 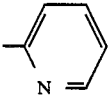 (furan) | Cl |
| CH₂ | Cl | H | 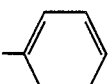 (pyridyl) | Cl |
| CHCH₃ | NHCN | H | 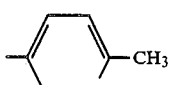 | Cl |
| CH₂ | Cl | H | 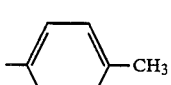 (–CH₃, pyridyl) | Cl |
| CH₂ | Cl | H | 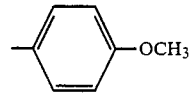 (–CH₃) | Cl |
| CH₂ | Cl | H | 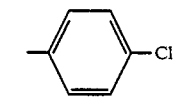 (–OCH₃) | Cl |
| CH₂ | Cl | H | 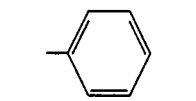 (–Cl) | Cl |
| CHCH₃ | CH₃ | H | phenyl | Cl |

The halogenated triazines of the formula (II) are known and/or can be prepared by processes which are known per se (compare Zh. Obshch. Khim. 42 (1972), 2280–2284, cited in Chem. Abstracts 78 (1973), 72558w).

The compounds of the formula (II) are obtained by a process in which the corresponding dihalogenated or trihalogenated triazines, such as, for example, 2,4,6-trichloro-s-triazine ("cyanuric chloride") or 2,4-dichloro-6-methyl-s-triazine or 2,4-dichloro-6-cyanoamino-s-triazine are reacted with suitable amines, such as, for example, benzylamine, 2-phenyl-ethylamine, R- or S-or R/S-1-phenyl-ethylamine or 3-pyridyl-methylamine, if appropriate in the presence of a diluent, such as, for example, tetrahydrofuran, and if appropriate in the presence of an acid acceptor, such as, for example, triethylamine or ethyl-diisopropylamine, at temperatures between +30° C. and −80° C.

Formula (III) provides a general definition of the amino compounds furthermore to be used as starting substances in process (a).

In formula (III), $A^2$, Q, $R^4$ and $R^5$ preferably or particularly or especially preferably have those meanings which have already been mentioned above as preferred or as particularly preferred or as especially preferred for $A^2$, Q, $R^4$ and $R^5$ in the context of the description of the compounds of the formula (I) according to the invention.

Examples of the starting substances of the formula (III) are listed in the following Table 2.

TABLE 2

Examples of the starting substances of formula (III)

$$H-N-A^2-Q-R^5$$
$$\;\;\;\;\;\;\;\;|$$
$$\;\;\;\;\;\;\;R^4$$

(III)

| A² | Q | R⁴ | R⁵ |
|---|---|---|---|
| CH₂ | O | H | CH₃ |
| CH₂CH₂ | O | H | CH₃ |

TABLE 2-continued

Examples of the starting substances of the formula (III)

$$H-N-A^2-Q-R^5 \quad (III)$$
$$\quad | \quad$$
$$\quad R^4$$

| A² | Q | R⁴ | R⁵ |
|---|---|---|---|
| CH₂CH₂ | S | H | CH₃ |
| CH₂CH₂ | NH | H | CH₃ |
| CH₂CH₂ | NCH₃ | H | CH₃ |
| CH₂CH₂ | O | CH₃ | CH₃ |
| CH₂CH₂ | S | H | C₂H₅ |
| CH₂CH₂ | O | H | C₂H₅ |
| (CH₂)₃ | O | H | CH₃ |
| (CH₂)₃ | O | H | C₂H₅ |
| CH₂CH₂ | O | CH₃ | C₂H₅ |
| CHCH₂<br>\|<br>CH₃ | O | H | CH₃ |

The amino compounds of the formula (III) are known synthesis chemicals.

Formula (IV) provides a general definition of the halogenated triazines to be used as starting substances in process (b) according to the invention. In formula (IV), A², Q, R¹, R⁴ and R⁵ preferably or particularly or especially preferably have those meanings which have already been mentioned as preferred or as particularly preferred or as especially preferred for A², Q, R¹, R⁴ or R⁵ in the context of the description of the compounds of the formula (I) according to the invention, and Y preferably represents fluorine, chlorine or bromine, in particular chlorine.

Examples of the starting substances of the formula (IV) are listed in the following Table 3.

TABLE 3

Examples of the starting substances of the formula (IV)

| A² | Q | R¹ | R⁴ | R⁵ | Y |
|---|---|---|---|---|---|
| CH₂ | O | Cl | H | CH₃ | Cl |
| CH₂CH₂ | O | Cl | H | CH₃ | Cl |
| CH₂CH₂ | S | Cl | H | CH₃ | Cl |
| CH₂CH₂ | NH | Cl | H | CH₃ | Cl |
| CH₂CH₂ | NCH₃ | Cl | H | CH₃ | Cl |
| CH₂CH₂ | O | Cl | CH₃ | CH₃ | Cl |
| CH₂CH₂ | O | Cl | H | C₂H₅ | Cl |
| (CH₂)₃ | O | Cl | H | CH₃ | Cl |
| (CH₂)₃ | O | Cl | H | C₂H₅ | Cl |
| CH₂ | O | Cl | H | C₂H₅ | Cl |
| CH₂CH₂ | O | Cl | H | C₂H₅ | Cl |
| CH₂CH₂ | O | OCH₃ | H | CH₃ | Cl |
| CH₂CH₂ | O | SCH₃ | H | CH₃ | Cl |
| CH₂CH₂ | O | CH₃ | H | CH₃ | Cl |
| CH₂CH₂ | O | NHCN | H | CH₃ | Cl |
| CH₂CH₂ | O | Cl | CH₃ | C₂H₅ | Cl |
| CH—CH₂<br>\|<br>CH₃ | O | Cl | H | CH₃ | Cl |

The halogenated triazines of the formula (IV) are known and/or can be prepared by processes which are known per se (compare Swiss Patent Specification 605,853, cited in Chem. Abstracts 90 (1979), 54988e; and East German Patent Specification 51,646, cited in Chem. Abstracts 66 (1967), 105005w).

The compounds of the formula (IV) are obtained by a process in which corresponding dihalogenated or trihalogenated triazines, such as, for example, 2,4,6-trichloro-s-triazine ("cyanuric chloride") or 2,4-dichloro-6-methyl-s-triazine or 2,4-dichloro-6-cyanoamino-s-triazine, are reacted with suitable amines, such as, for example, 2-methoxyethylamine, 2-ethoxy-ethylamine, 2-methylthioethylamine, 2-methylamino-ethylamine or 3-methoxy-propylamine, if appropriate in the presence of a diluent, such as, for example, tetrahydrofuran, and if appropriate in the presence of an acid acceptor, such as, for example, triethylamine or ethyl-diisopropylamine, at temperatures between +30° C. and −80° C.

Formula (V) provides a general definition of the amino compounds furthermore to be used as starting substances in process (b).

In formula (V), A¹, R² and R³ preferably or particularly or especially preferably have those meanings which have already been mentioned above as preferred or as particularly preferred or as especially preferred for A¹, R² and R³ in the context of the description of the compounds of the formula (I) according to the invention.

Examples of the starting substances of the formula (V) are listed in the following Table 4.

TABLE 4

Examples of the starting substances of the formula (V)

$$\quad R^2 \quad (V)$$
$$\quad | \quad$$
$$H-N-A^1-R^3$$

| A¹ | R² | R³ |
|---|---|---|
| CH₂ | H | phenyl |
| CHCH₃ | H | phenyl |
| CH₂ | CH₃ | phenyl |
| CH₂ | H | pyridyl |
| CH₂ | H | chloropyridyl |
| CHCH₃ | H | fluorophenyl |

TABLE 4-continued

Examples of the starting substances of the formula (V)

$$H-\overset{R^2}{\underset{|}{N}}-A^1-R^3 \quad (V)$$

| $A^1$ | $R^2$ | $R^3$ |
|---|---|---|
| CHCH$_3$ | H | -C$_6$H$_4$-Cl |
| CH$_2$CH$_2$ | H | -C$_6$H$_5$ |
| CH$_2$ | H | 2-furyl |
| CH$_2$ | H | 5-methyl-2-furyl |
| CH$_2$ | H | 2-pyridyl |
| CH$_2$ | H | 6-methyl-2-pyridyl |
| CH$_2$ | H | -C$_6$H$_4$-OCH$_3$ |
| CH$_2$ | H | -C$_6$H$_4$-CH$_3$ |
| CH$_2$ | H | -C$_6$H$_4$-Cl |

The amino compounds of the formula (V) are known and/or can be prepared by processes which are known per se (compare European Patent A-192,060).

Formula (VI) provides a general definition of the halogenated triazines to be used as starting substances in process (c) according to the invention. In formula (VI), $A^1$, $A^2$, Q, $R^2$, $R^3$, $R^4$ and $R^5$ preferably or particularly or especially preferably have those meanings which have already been mentioned as preferred or as particularly preferred or as especially preferred for $A^1$, $A^2$, Q, $R^2$, $R^3$, $R^4$ and $R^5$ in the context of the description of the compounds of the formula (I) according to the invention, and Z preferably represents fluorine, chlorine or bromine, in particular chlorine.

Examples of the starting substances of the formula (VI) are listed in the following Table 5.

TABLE 5

Examples of the starting substances of the formula (VI)

(VI)

| $A^1$ | $A^2$ | Q | $R^2$ | $R^3$ | $R^4$ | $R^5$ | Z |
|---|---|---|---|---|---|---|---|
| CH$_2$ | CH$_2$CH$_2$ | O | H | phenyl | H | CH$_3$ | Cl |
| CH$_2$CH$_2$ | CH$_2$CH$_2$ | O | H | phenyl | H | CH$_3$ | Cl |

TABLE 5-continued

Examples of the starting substances of the formula (VI)

$$\underset{R^4}{\overset{R^2}{\underset{|}{N}}}-A^1-R^3$$

(Structure VI: Z-C(=N-)-N=C(N-A^1-R^3 with R^2)-N=C(N-A^2-Q-R^5 with R^4), triazine ring)

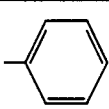

| A¹ | A² | Q | R² | R³ | R⁴ | R⁵ | Z |
|---|---|---|---|---|---|---|---|
| CHCH₃ | CH₂CH₂ | O | H | phenyl | H | CH₃ | Cl |
| CHCH₃ | CH₂CH₂ | O | H | phenyl | H | C₂H₅ | Cl |
| CH₂ | CH₂CH₂ | O | CH₃ | phenyl | H | CH₃ | Cl |
| CHCH₃ | (CH₂)₃ | O | H | phenyl | H | CH₃ | Cl |
| CH₂ | CH₂CH₂ | O | H | 3-pyridyl | H | CH₃ | Cl |
| CH₂ | CH₂CH₂ | O | H | 6-chloro-3-pyridyl | H | CH₃ | Cl |
| CHCH₃ | CH₂CH₂ | O | H | 4-fluorophenyl | H | CH₃ | Cl |
| CHCH₃ | CH₂CH₂ | O | H | 4-chlorophenyl | H | CH₃ | Cl |
| CH₂ | CH₂CH₂ | O | H | 2-furyl | H | CH₃ | Cl |
| CH₂ | CH₂CH₂ | O | H | 2-pyridyl | H | C₂H₅ | Cl |
| CH₂ | CH₂CH₂ | O | H | 6-methyl-3-pyridyl | H | CH₃ | Cl |

TABLE 5-continued

Examples of the starting substances of the formula (VI)

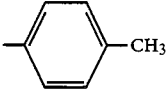

(VI)

| $A^1$ | $A^2$ | Q | $R^2$ | $R^3$ | $R^4$ | $R^5$ | Z |
|---|---|---|---|---|---|---|---|
| $CH_2$ | $CH_2CH_2$ | O | H | 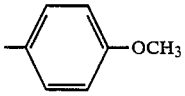 —$CH_3$ | H | $C_2H_5$ | Cl |
| $CH_2$ | $CH_2CH_2$ | O | H | 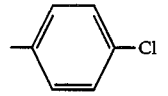 —$OCH_3$ | H | $CH_3$ | Cl |
| $CH_2$ | $CH_2CH_2$ | O | H | 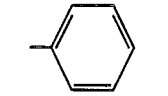 —Cl | H | $CH_3$ | Cl |
| $CHCH_3$ | $CH_2CH_2$ | O | H | 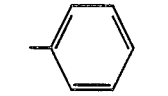 | $CH_3$ | $CH_3$ | Cl |
| $CHCH_3$ | $CH_2$ | O | H | 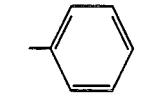 | H | $CH_3$ | Cl |
| $CH_2$ | $\overset{\|}{C}HCH_2$<br>$CH_3$ | O | H | 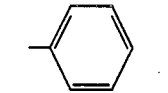 | H | $CH_3$ | Cl |
| $CHC_2H_5$ | $CH_2CH_2$ | O | H | (phenyl) | H | $C_2H_5$ | Cl |

The starting substances of the formula (VI) are also active compounds according to the invention which are included in the range of definitions of the formula (I). They can be prepared by processes (a) and (b) according to the invention.

The alkylamines, dialkylamines, alkanols or alkanethiols to be employed in process (c), preferably each with up to 4 carbon atoms, in particular with 1 or 2 carbon atoms, such as, for example, methylamine, ethylamine, dimethylamine, methanol, ethanol, methanethiol and ethanethiol, and sodium salts or potassium salts thereof, are known synthesis chemicals.

Formula (VII) provides a general definition of the mercaptotriazines to be used as starting substances in process (d) according to the invention. In formula (VII), $A^1$, $A^2$, Q, $R^2$, $R^3$, $R^4$ and $R^5$ preferably or particularly or especially preferably have those meanings which have already been mentioned as preferred or as particularly preferred or as especially preferred for $A^1$, $A^2$, Q, $R^2$, $R^3$, $R^4$ and $R^5$ in the context of the description of the compounds of the formula (I) according to the invention.

Examples of the starting substances of the formula (VII) are listed in the following Table 6.

TABLE 6

Examples of the starting substances of the formula (VII)

$$\begin{array}{c} R^2 \\ | \\ N-A^1-R^3 \\ \diagup \\ HS-\langle \quad N \\ \diagdown \\ N = \\ \quad N-A^2-Q-R^5 \\ \quad | \\ \quad R^4 \end{array} \quad (VII)$$

| $A^1$ | $A^2$ | Q | $R^2$ | $R^3$ | $R^4$ | $R^5$ |
|---|---|---|---|---|---|---|
| $CH_2$ | $CH_2CH_2$ | O | H | —C$_6$H$_5$ | H | $CH_3$ |
| $CH_2CH_2$ | $CH_2CH_2$ | O | H | —C$_6$H$_5$ | H | $CH_3$ |
| $CHCH_3$ | $CH_2CH_2$ | O | H | —C$_6$H$_5$ | H | $CH_3$ |
| $CHCH_3$ | $CH_2CH_2$ | O | H | —C$_6$H$_5$ | H | $C_2H_5$ |
| $CH_2$ | $CH_2CH_2$ | O | $CH_3$ | —C$_6$H$_5$ | H | $CH_3$ |
| $CHCH_3$ | $(CH_2)_3$ | O | H | —C$_6$H$_5$ | H | $CH_3$ |
| $CHCH_3$ | $CH_2CH_2$ | O | H | —C$_6$H$_4$—F | H | $C_2H_5$ |
| $CHCH_3$ | $CH_2CH_2$ | O | H | —C$_6$H$_4$—Cl | H | $C_2H_5$ |
| $CHCH_3$ | $CH_2CH_2$ | O | H | —C$_6$H$_4$—CH$_3$ | H | $C_2H_5$ |
| $CHCH_3$ | $CH_2CH_2$ | O | H | —C$_6$H$_4$—OCH$_3$ | H | $CH_3$ |
| $CH_2$ | $CH_2CH_2$ | O | H | —(pyridyl) | H | $C_2H_5$ |
| $CH_2$ | $CH_2CH_2$ | O | H | 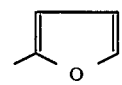 | H | $C_2H_5$ |

The mercaptotriazines of the formula (VII) were hitherto unknown from the Literature.

The new compounds of the formula (VII) are obtained by a process in which halogenated triazines of the formula (VI)—above—are initially reacted with thiourea, preferably in the presence of a diluent, such as, for example, dioxane, at temperatures between 0° C. and 150° C., and are then reacted with an aqueous alkali hydroxide solution, preferably 2N sodium hydroxide solution, at temperatures between 50° C. and 120° C. and worked up by customary methods.

The halogenoalkyl compounds to be employed in process (d), preferably chloro- or bromo-alkanes with 1 to 4 carbon atoms, in particular with 1 or 2 carbon atoms and substituted by flourine or cyano, such as, for example, chlorodifluoromethane, chloroacetonitrile, bromoacetonitrile or bromopropionitrile, are known synthesis chemicals.

Process (a) according to the invention for the preparation of the new substituted triazines of the formula (I) is preferably carried out using diluents. Possible diluents here are virtually all inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide.

Acid acceptors which can be used in process (a) according to the invention are all acid-binding agents which can usually be employed for such reactions. Preferred possible acid-binding agents are alkali metal hydroxides, such as, for example, sodium hydroxide and potassium hydroxide, alkaline earth metal hydroxides, such as, for example, calcium hydroxide, alkali metal carbonates and alcoholates, such as sodium and potassium carbonate and sodium and potassium tert-butylate, and furthermore aliphatic, aromatic or heterocyclic amines, for example triethylamine, trimethylamine, ethyl-diisopropylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO). The starting substances of the formula (III) can also be used as acid acceptors.

The reaction temperatures can be varied within a relatively wide range in process (a) according to the invention. The reaction is in general carried out at temperatures between −30° C. and +50° C., preferably at temperatures between −20° C and +40° C.

Process (a) according to the invention is in general carried out under normal pressure. However, it is also possible for the process to be carried out under increased or reduced pressure.

For carrying out process (a) according to the invention, the starting substances of the formulae (II) and (III) are in general employed in approximately equimolar amounts. If separate acid acceptors are dispensed with, about 2 mols of amino compound of the formula (III) are in general employed per mol of triazine of the formula (II).

The reaction components are in general combined at room temperature or with cooling and the reaction mixture is stirred until the reaction has ended. Working up can be carried out by customary methods.

Process (b) according to the invention for the preparation of the new substituted triazines of the formula (I) is preferably carried out using diluents such as are mentioned above for process (a).

Process (b) is preferably carried out using acid acceptors such as are mentioned above for process (a). The starting substances of the formula (V) can also be used as acid acceptors.

The reaction temperatures can be varied within a relatively wide range in process (b) according to the invention. The reaction is in general carried out at temperatures between −30° C. and +50° C., preferably at temperatures between −20° C. and +40° C.

Process (b) according to the invention is in general carried out under normal pressure. However, it is also possible to carry out the process under increased or reduced pressure.

For carrying out process (b) according to the invention, the starting substances of the formulae (IV) and (V) are in general employed in approximately equimolar amounts. If separate acid acceptors are dispensed with, about 2 mols of amino compound of the formula (V) are in general employed per mol of triazine of the formula (IV).

The reaction components are in general combined at room temperature or with cooling and the reaction mixture is stirred until the reaction has ended. Working up can be carried out by customary methods.

Process (c) according to the invention for the preparation of the new substituted triazines of the formula (I) is preferably carried out using diluents such as are mentioned above for process (a).

Process (c) can be carried out using acid acceptors such as are mentioned above for process (a). However, in the case of reaction to form alkoxythio compounds or alkylthio compounds, the sodium salts or potassium salts of the alkanols or alkanethiols required for process (c) are preferably employed, separate acid acceptors being dispensed with.

The reaction temperatures can be varied within a relatively wide range in process (c) according to the invention. The reaction is in general carried out at temperatures between −20° C. and +80° C., preferably at temperatures between 0° C. and 50° C.

Process (c) according to the invention is in general carried out under normal pressure. However, it is also possible to carry out the process under increased or reduced pressure.

For carrying out process (c) according to the invention, in general between 1 and 2 mols, preferably between 1.0 and 1.2 mols, of an alkanol or alkanethiol or alkali metal salts thereof are employed per mol of starting compound of the formula (VI).

The reaction components are in general combined at room temperature or with cooling and the reaction mixture is stirred until the reaction has ended. Working up can be carried out by customary methods.

Process (d) according to the invention for the preparation of the new substituted triazines of the formula (I) is preferably carried out using diluents such as are mentioned above for process (a). However, water and alcohols, such as, for example, methanol, ethanol, propanol, isopropanol, butanol, isobutanol, sec-butanol or tert-butanol can also be used as diluents.

Process (d) is preferably carried out using acid acceptors such as are mentioned above for process (a).

The reaction temperatures can be varied within a relatively wide range in process (d) according to the invention. The reaction is in general carried out at temperatures between 0° C. and 100° C., preferably at temperatures between 10° C. and 80° C.

Process (d) according to the invention is in general carried out under normal pressure. However, it is also possible to carry out the process under increased or reduced pressure.

For carrying out process (d) according to the invention, in general between 1 and 10 mols, preferably between 1 and 3 mols, of halogenoalkyl compound of the formula (VIII) are employed per mol of starting compound of the formula (VII).

Preferably, the mercaptotriazine of the formula (VII) is initially introduced with a diluent and an acid acceptor, and the halogenoalkyl compound of the formula (VIII) is slowly metered in. Working up can be carried out by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Argostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total conbating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating monocotyledon and dicotyledon weeds in monocotyledon crops, in particular by the post-emergence method.

They are well tolerated by corn, barley and wheat and are clearly more effective against monocotyledon and dicotyledon weeds than the known atrazine.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as finely divided silica, alumina and silicates, as solid carriers for granules there are suitable: for example crushed and fractioned natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, ready-to-use formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugarbeet and 4-amino-6-(1,1-dimethylethyl)-3-methylthio-1,2,4-triazin-5(4H)-one for combating weeds in soybeans; and furthermore also 2,4-dichlorophenoxyacetic acid; 2,4-dichlorophenoxypropionic acid; 4-(2,4-dichlorophenoxy)-butyric acid; (2-methyl-4-chlorophenoxy)-acetic acid; (4-chloro-2-methylphenoxy)-propionic acid; chloroacetic acid N-(methoxymethyl)-2,6-diethylanilide; 2-chloro-N-(2,6-dimethylphenyl)-N-[(1H)-pyrazol-1-ylmethyl]-acetamide; 2-ethyl-6-methyl-N-(1-methyl-2-methoxyethyl)-chloroacetanilide; N-(1-ethylpropyl)-3,4-dimethyl-2,6-dinitroaniline; 3,5-dibromo-4-hydroxybenzonitrile; 3,5-diiodo-4-hydroxybenzonitrile; N-methyl-2-(1,3-benzothiazol-2-yloxy)-acetanilide; methyl 3-[[[[(4-methoxy-6-methyl-1,3,5-triazin-2-yl)-amino]-carbonyl]-amino]-sulphonyl]-thiophene-2-carboxylate; 2-chloro-4-ethylamino-6-isopropylamino-1,3,5-triazine; 2-chloro-4-ethylamino-6-(3-cyanopropylamino)-1,3,5-triazine; 3-isopropyl-2,1,3-benzothiadiazin-4-one 2,2-dioxide and 0-(6-chloro-3-phenyl-pyridazin-4-yl) S-octyl thiocarbonate. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively wide range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

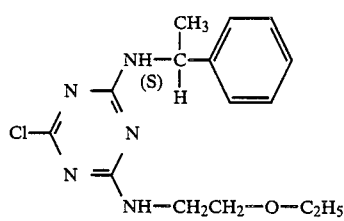

(Process (a))

A solution of 3.56 g (0.04 mol) of 2-ethoxyethylamine in 20 ml of tetrahydrofuran is added dropwise to a solution, cooled to −10° C., of 5.4 g (0.02 mol) of (S)-2,4-dichloro-6-(1-phenyl-ethylamino)-s-triazine in 50 ml of tetrahydrofuran in the course of about 20 minutes, with stirring. The reaction mixture is then stirred at −10° C. for 30 minutes and the product which is obtained as crystals is subsequently isolated by filtration with suction.

6.4 g (99% of theory) of (S)-2-chloro-4-(2-ethoxy-ethylamino)- 6-(1-phenyl-ethylamino)-s-triazine of melting point 103° C. are obtained.

EXAMPLE 2

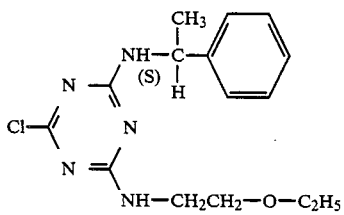

(Process (b))

A solution of 10.9 g (0.09 mol) of (S)-1-phenylethylamine in 100 ml of tetrahydrofuran and a solution of 9.1 g (0.09 mol) of triethylamine in 50 ml of tetrahydrofuran are added dropwise to a solution, cooled to −10° C., of 21.3 g (0.09 mol) of 2,4-dichloro-6-(2-ethoxyethylamino)-s-triazine in 100 ml of tetrahydrofuran, with stirring. After the cooling has been removed, the reaction mixture is stirred at −10° C. for about 60 minutes and is then concentrated under a waterpump vacuum, the residue is taken up in 50 ml of methylene chloride, the mixture is concentrated again and the residue is stirred with petroleum ether.

After filtration with suction, 17.4 g (60% of theory) of (S)-2-chloro-4-(2-ethoxy-ethylamino)-6-(1-phenylethylamino)-s-triazine of melting point 103° C. are obtained.

EXAMPLE 3

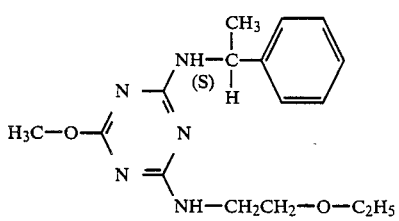

(Process (c))

A mixture of 1.6 g (0.005 mol) of (S)-2-chloro- 4-(2-ethoxy-ethylamino)-6-(1-phenyl-ethylamino)-s-triazine, 0.27 g (0.005 mol of sodium methanolate and 20 ml of tetrahydrofuran is stirred at 20° C. for about 20 hours. It is concentrated, the residue is taken up in water, the mixture is extracted with methylene chloride, the extraction solution is dried with sodium sulphate and filtered and the solvent is distilled off from the filtrate under a waterpump vacuum.

1.4 g (80% of theory) of (S)-2-methoxy-4-(2-ethoxyethylamino)-6-(1-phenyl-ethylamino)-s-triazine are obtained as an oily residue of refractive index $n_D 22 = 1.5610$.

The compounds of the formula (I) shown in the following Table 7 can be prepared analogously to Example 1, 2 and 3 and in accordance with the general description of processes (a), (b), (c) and (d) according to the invention.

TABLE 7

Examples of the compounds of the formula (I)

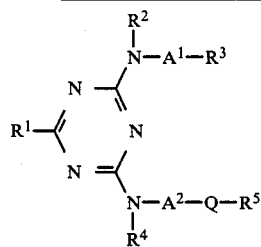

(I)

| Example No. | A¹ | A² | Q | R¹ | R² | R³ | R⁴ | R⁵ | Melting point or refractive index |
|---|---|---|---|---|---|---|---|---|---|
| 4 | (S)—CHCH₃ | CH₂CH₂ | O | Cl | H | C₆H₅ | H | CH₃ | 115° C. |
| 5 | (S)—CHCH₃ | (CH₂)₃ | O | Cl | H | C₆H₅ | H | CH₃ | 128° C. |
| 6 | (S)—CHCH₃ | CH₂CH₂ | O | SCH₃ | H | C₆H₅ | H | CH₃ |  |
| 7 | (S)—CHCH₃ | CH₂CH₂ | O | SCH₃ | H | C₆H₅ | H | C₂H₅ | (amorphous) |
| 8 | (S)—CHCH₃ | CH₂CH₂ | O | OCH₃ | H | C₆H₅ | H | CH₃ |  |
| 9 | (R)—CHCH₃ | CH₂CH₂ | O | Cl | H | C₆H₅ | H | C₂H₅ | 102° C. |
| 10 | (R/S)—CHCH₃ | CH₂CH₂ | O | Cl | H | C₆H₅ | H | C₂H₅ |  |
| 11 | (S)—CHCH₃ | CH₂CH₂ | O | Cl | H | C₆H₅ | CH₃ | CH₃ | (amorphous) |
| 12 | —(CH₂)₃— | CH₂CH₂ | O | Cl | H | C₆H₅ | H | C₂H₅ | 146° C. |
| 13 | —(CH₂)₃— | CH₂CH₂ | O | Cl | H | C₆H₅ | H | CH₃ | 159° C. |
| 14 | —(CH₂)₃— | —(CH₂)₃— | O | Cl | H | C₆H₅ | H | CH₃ | 154° C. |

TABLE 7-continued

Examples of the compounds of the formula (I)

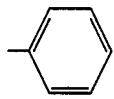
(I)

| Example No. | A¹ | A² | Q | R¹ | R² | R³ | R⁴ | R⁵ | Melting point or refractive index |
|---|---|---|---|---|---|---|---|---|---|
| 15 | (R)—CHCH₃ | CH₂CH₂ | O | OCH₃ | H | 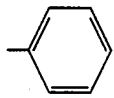 | H | C₂H₅ | (amorphous) |
| 16 | (R/S)—CH—CH₂—<br>$\quad$ $\vert$<br>$\quad$ C₆H₅ | CH₂CH₂ | O | Cl | H | 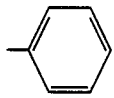 | H | CH₃ | 104° C. |
| 17 | (R/S)—CH—CH₂<br>$\quad$ $\vert$<br>$\quad$ C₆H₅ | CH₂CH₂ | O | Cl | H | 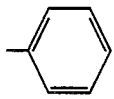 | H | C₂H₅ | 43° C. |
| 18 | (R/S)—CH—CH₂<br>$\quad$ $\vert$<br>$\quad$ C₆H₅ | —(CH₂)₃— | O | Cl | H | 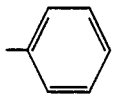 | H | CH₃ | 41° C. |
| 19 | (S)—CHCH₃ | CH₂CH₂ | S | Cl | H | 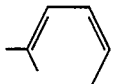 | H | C₂H₅ | 55° C. |
| 20 | CH₂ | CH₂CH₂ | O | Cl | H | 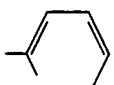 | H | CH₃ | 137° C. |
| 21 | CH₂ | CH₂CH₂ | O | Cl | H | 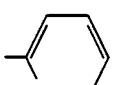 | H | C₂H₅ | 125° C. |
| 22 | CH₂ | —(CH₂)₃— | O | Cl | H | 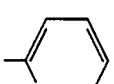 | H | C₂H₅ | 134° C. |
| 23 | CH₂CH₂ | CH₂CH₂ | O | Cl | H | 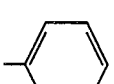 | H | CH₃ | 143° C. |
| 24 | CH₂CH₂ | CH₂CH₂ | O | Cl | H | 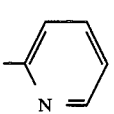 | H | C₂H₅ | 147° C. |
| 25 | CH₂CH₂ | —(CH₂)₃— | O | Cl | H |  | H | CH₃ | 157° C. |

TABLE 7-continued

Examples of the compounds of the formula (I)

$$\begin{array}{c} R^2 \\ | \\ N-A^1-R^3 \\ N \\ R^1 \diagdown \diagup N \\ N \\ N-A^2-Q-R^5 \\ | \\ R^4 \end{array}$$ (I)

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 26 | $CH_2$ | $CH_2CH_2$ | O | Cl | H | 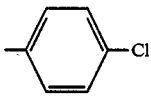 | H | $CH_3$ | 103° C. |
| 27 | (S)—$CHCH_3$ | —$(CH_2)_3$— | O | Cl | H |  | H | $C_2H_5$ | 69° C. |
| 28 | (S)—$CHCH_3$ | —$(CH_2)_3$— | O | Cl | H |  | H | $C_4H_9$ | 53° C. |
| 29 | $CH_2$ | —$(CH_2)_3$— | O | Cl | H | 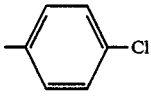 | H | $CH_3$ | 194° C. |
| 30 | $CH_2$ | $CH_2CH_2$ | O | Cl | H | 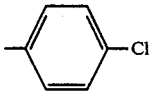 | H | $C_2H_5$ | 196° C. |
| 31 | $CH_2CH_2$ | $CH_2CH_2$ | O | Cl | H | 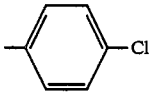 | H | $CH_3$ | 196° C. |
| 32 | $CH_2CH_2$ | $CH_2CH_2$ | O | Cl | H | 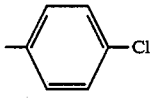 | H | $C_2H_5$ | 196° C. |
| 33 | $CH_2CH_2$ | —$(CH_2)_3$— | O | Cl | H | 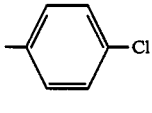 | H | $CH_3$ | 197° C. |
| 34 | (S)—$CHCH_3$ | $CH_2CH_2$ | O | $SCH(CH_3)_2$ | H |  | H | $C_2H_5$ | $n_D^{20} = 1,5625$ |
| 35 | (S)—$CHCH_3$ | $CH_2CH_2$ | O | $SC_2H_5$ | H |  | H | $C_2H_5$ | (amorphous) |
| 36 | (S)—$CHCH_3$ | $CH_2CH_2$ | O | $OC_2H_5$ | H |  | H | $C_2H_5$ | (amorphous) |

TABLE 7-continued

Examples of the compounds of the formula (I)

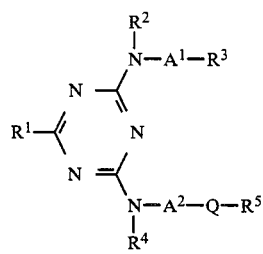

(I)

| Example No. | A¹ | A² | Q | R¹ | R² | R³ | R⁴ | R⁵ | Melting point or refractive index |
|---|---|---|---|---|---|---|---|---|---|
| 37 | (S)—CHCH₃ | CH₂CH₂ | O | OCH(CH₃)₂ | H | phenyl | H | C₂H₅ | (amorphous) |
| 38 | (S)—CHCH₃ | CH₂CH₂ | O | Cl | CH₃ | phenyl | H | C₂H₅ | (amorphous) |
| 39 | (S)—CHCH₃ | CH₂CH₂ | O | NHCH₃ | H | phenyl | H | C₂H₅ | (amorphous) |
| 40 | CH₂ | CH₂CH₂ | O | Cl | H | 2-Cl-pyridyl | H | C₂H₅ | 176° C. |
| 41 | CH₂ | CH₂CH₂ | O | Cl | H | 4-OCH₃-phenyl | H | CH₃ | 172°C. |
| 42 | CH₂ | CH₂CH₂ | O | Cl | H | 4-CF₃-phenyl | H | CH₃ | 219° C. |
| 43 | CH₂ | CH₂CH₂ | O | Cl | H | 4-CF₃-phenyl | H | C₂H₅ | 198° C. |
| 44 | CH₂ | —(CH₂)₃— | O | Cl | H | 4-CF₃-phenyl | H | CH₃ | 214° C. |
| 45 | CH₂ | CH₂CH₂ | O | Cl | H | 4-Br-phenyl | H | CH₃ | 184° C. |
| 46 | CH₂ | CH₂CH₂ | O | Cl | H | 4-Br-phenyl | H | C₂H₅ | 191° C. |

TABLE 7-continued

Examples of the compounds of the formula (I)

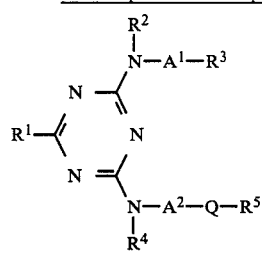

(I)

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 47 | $CH_2$ | $-(CH_2)_3-$ | O | Cl | H | ⟨4-Br-phenyl⟩ | H | $CH_3$ | 205° C. |
| 48 | $CH_2$ | $CH_2CH_2$ | O | Cl | H | ⟨4-C(CH_3)_3-phenyl⟩ | H | $CH_3$ | 176° C. |
| 49 | $CH_2$ | $CH_2CH_2$ | O | Cl | H | ⟨4-C(CH_3)_3-phenyl⟩ | H | $C_2H_5$ | 165° C. |
| 50 | $CH_2$ | $-(CH_2)_3-$ | O | Cl | H | ⟨4-C(CH_3)_3-phenyl⟩ | H | $CH_3$ | 176° C. |
| 51 | $CH_2$ | $CH_2CH_2$ | O | Cl | H | ⟨3,4-methylenedioxyphenyl⟩ | H | $CH_3$ | 178° C. |
| 52 | $CH_2$ | $CH_2CH_2$ | O | Cl | H | ⟨3,4-methylenedioxyphenyl⟩ | H | $C_2H_5$ | 178° C. |
| 53 | $CH_2$ | $-(CH_2)_3-$ | O | Cl | H | ⟨3,4-methylenedioxyphenyl⟩ | H | $CH_3$ | 182° C. |
| 54 | $CH_2CH_2$ | $CH_2CH_2$ | O | Cl | H | ⟨4-OCH_3-phenyl⟩ | H | $CH_3$ | 181° C. |
| 55 | $CH_2CH_2$ | $CH_2CH_2$ | O | Cl | H | ⟨4-OCH_3-phenyl⟩ | H | $C_2H_5$ | 182° C. |
| 56 | $-CH_2CH(CH_3)-$ | $CH_2CH_2$ | O | Cl | H | ⟨phenyl⟩ | H | $CH_3$ | 136° C. |

TABLE 7-continued

Examples of the compounds of the formula (I)

$$\begin{array}{c} R^2 \\ | \\ N-A^1-R^3 \\ N \diagup \diagdown \\ \| \\ R^1 \diagdown \diagup N \\ N \\ \| \\ N-A^2-Q-R^5 \\ | \\ R^4 \end{array} \quad (I)$$

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 57 | −CH$_2$CH−<br>\|<br>CH$_3$ | CH$_2$CH$_2$ | O | Cl | H | phenyl | H | C$_2$H$_5$ | 138° C. |
| 58 | −CH$_2$CH−<br>\|<br>CH$_3$ | −(CH$_2$)$_3$− | O | Cl | H | phenyl | H | CH$_3$ | 135° C. |
| 59 | −CHCH$_2$CH$_2$<br>\|<br>CH$_3$ | CH$_2$CH$_2$ | O | Cl | H | phenyl | H | CH$_3$ | (amorphous) |
| 60 | −CHCH$_2$CH$_2$<br>\|<br>CH$_3$ | CH$_2$CH$_2$ | O | Cl | H | phenyl | H | C$_2$H$_5$ | (amorphous) |
| 61 | CH$_2$CH$_2$ | −(CH$_2$)$_3$− | O | Cl | H | phenyl | H | CH$_3$ | (amorphous) |
| 62 | CH$_2$ | CH$_2$CH$_2$ | O | Cl | H | naphthyl | H | CH$_3$ | 154° C. |
| 63 | CH$_2$ | CH$_2$CH$_2$ | O | Cl | H | naphthyl | H | C$_2$H$_5$ | 160° C. |
| 64 | CH$_2$ | −(CH$_2$)$_3$− | O | Cl | H | naphthyl | H | CH$_3$ | 152° C. |
| 65 | CH$_2$ | CH$_2$CH$_2$ | O | OCH$_3$ | H | 4-chlorophenyl | H | C$_2$H$_5$ | 99° C. |

TABLE 7-continued

Examples of the compounds of the formula (I)

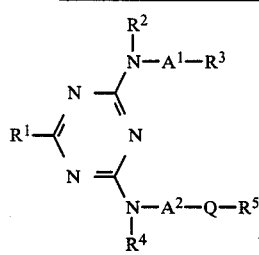

| Example No. | A¹ | A² | Q | R¹ | R² | R³ | R⁴ | R⁵ | Melting point or refractive index |
|---|---|---|---|---|---|---|---|---|---|
| 66 | (S)—CHCH₃ | CH₂CH₂ | O | NH₂ | H | phenyl | H | C₂H₅ | (amorphous) |
| 67 | CH₂ | —(CH₂)₃— | O | Cl | H | 2-Cl-phenyl | H | CH₃ | 165° C. |
| 68 | CH₂ | —(CH₂)₃— | O | Cl | H | 4-OCH₃-phenyl | H | CH₃ | 176° C. |
| 69 | CH₂CH₂ | —(CH₂)₃— | O | Cl | H | 4-F-phenyl | H | CH₃ | 212° C. |
| 70 | CH₂CH₂ | —(CH₂)₃— | O | Cl | H | 4-OCH₃-phenyl | H | CH₃ | 187–190° C. |
| 71 | CH₂CH₂ | —(CH₂)₃— | O | Cl | H | 3-OCH₃-phenyl | H | CH₃ | 138–140° C. |
| 72 | CH₂CH₂ | —(CH₂)₃— | O | Cl | H | 2-Cl-phenyl | H | CH₃ | 177° C. |
| 73 | (R/S)—CHCH₃ | —(CH₂)₃— | O | Cl | H | 4-CH₃-phenyl | H | CH₃ | 78–80° C. |
| 74 | (R/S)—CHCH₃ | —(CH₂)₃— | O | Cl | H | 3,4-diCl-phenyl | H | CH₃ | 86° C. |

TABLE 7-continued

Examples of the compounds of the formula (I)

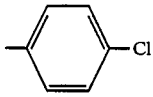

(I)

| Example No. | A¹ | A² | Q | R¹ | R² | R³ | R⁴ | R⁵ | Melting point or refractive index |
|---|---|---|---|---|---|---|---|---|---|
| 75 | (R/S)—CHCH₃ | —(CH₂)₃— | O | Cl | H | 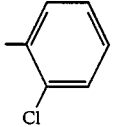 | H | CH₃ | 90–94° C. |
| 76 | CH₂ | —(CH₂)₃— | O | OCH₃ | H | 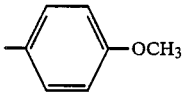 | H | CH₃ | 74° C. |
| 77 | CH₂ | —(CH₂)₃— | O | OCH₃ | H | 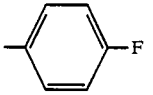 | H | CH₃ | 65° C. |
| 78 | CH₂CH₂ | —(CH₂)₃— | O | OCH₃ | H | 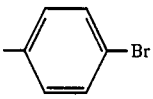 | H | CH₃ | 100° C. |
| 79 | (R/S)—CHCH₃ | —(CH₂)₃— | O | Cl | H | 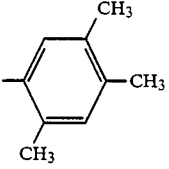 | H | CH₃ | 95–96° C. |
| 80 | (R/S)—CHCH₃ | —(CH₂)₃— | O | Cl | H | 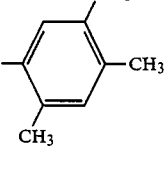 | H | CH₃ | 72–74° C. |
| 81 | (R/S)—CHCH₃ | —(CH₂)₃— | O | Cl | H | 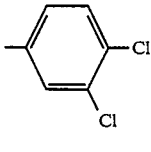 | H | CH₃ | 117–120° C. |
| 82 | (R/S)—CHCH₃ | —(CH₂)₃— | O | OCH₃ | H | 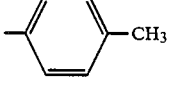 | H | CH₃ | $n_D^{21}$ = 1.5759 |
| 83 | (R/S)—CHCH₃ | —(CH₂)₃— | O | OCH₃ | H |  | H | CH₃ | 72–74° C. |

TABLE 7-continued

Examples of the compounds of the formula (I)

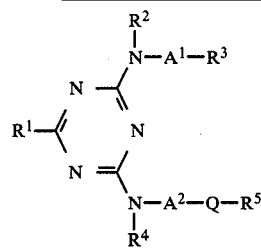

(I)

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 84 | $CH_2CH_2$ | $-(CH_2)_3-$ | O | Cl | H | 3-CF₃-phenyl | H | $CH_3$ | 185–186° C. |
| 85 | (R/S)—CHCH₃ | $-(CH_2)_3-$ | O | $OCH_3$ | H | 4-Cl-phenyl | H | $CH_3$ | $n_D^{21} = 1.5650$ |
| 86 | $CH_2CH_2$ | $-(CH_2)_3-$ | O | Cl | H | 3,4-diCl-phenyl | H | $CH_3$ | 200–202° C. |
| 87 | (R/S)—CHCH₃ | $-(CH_2)_3-$ | O | Cl | H | 1-naphthyl | H | $CH_3$ | 60° C. |
| 88 | (R/S)—CHCH₃ | $CH_2CH_2$ | O | Cl | H | 4-F-phenyl | H | $C_2H_5$ | $n_D^{21} = 1.5621$ |
| 89 | $CH_2$ | $-(CH_2)_3-$ | O | Cl | H | 2,5-diOCH₃-phenyl | H | $CH_3$ | 131–133° C. |
| 90 | $CH_2CH_2$ | $CH_2CH_2$ | O | Cl | H | 4-CH₃-phenyl | H | $C_2H_5$ | 203° C. |
| 91 | $CH_2CH_2$ | $CH_2CH_2$ | O | Cl | H | 2,4-diCl-phenyl | H | $C_2H_5$ | 201° C. |
| 92 | (R/S)—CHCH₃ | $CH_2CH_2$ | O | Cl | H | 3,4-diCl-phenyl | H | $C_2H_5$ | 80–84° C. |

TABLE 7-continued

Examples of the compounds of the formula (I)

$$\text{(I)}$$

Formula (I):
$R^1$ on triazine ring with two N–A groups bearing $NR^2R^3$ and $NR^4$–$A^2$–Q–$R^5$ substituents.

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 93 | (R/S)—CHCH$_3$ | CH$_2$CH$_2$ | O | Cl | H | 4-CH$_3$-C$_6$H$_4$ | H | C$_2$H$_5$ | $n_D^{21}$ = 1.5700 |
| 94 | CH$_2$ | CH$_2$CH$_2$ | O | Cl | H | 2-Cl-C$_6$H$_4$ | H | C$_2$H$_5$ | 160° C. |
| 95 | (R/S)—CHCH$_3$ | CH$_2$CH$_2$ | O | Cl | H | 4-Cl-C$_6$H$_4$ | H | C$_2$H$_5$ | 58° C. |
| 96 | CH$_2$CH$_2$ | CH$_2$CH$_2$ | O | Cl | H | 4-F-C$_6$H$_4$ | H | C$_2$H$_5$ | 208–211° C. |
| 97 | CH$_2$ | CH$_2$CH$_2$ | O | Cl | H | 4-OCH$_3$-C$_6$H$_4$ | H | C$_2$H$_5$ | 195° C. |
| 98 | CH$_2$CH$_2$ | CH$_2$CH$_2$ | O | Cl | H | 2,4-F$_2$-C$_6$H$_3$ | H | C$_2$H$_5$ | 114° C. |
| 99 | CH$_2$CH$_2$ | CH$_2$CH$_2$ | O | Cl | H | 2-CF$_3$-C$_6$H$_4$ | H | C$_2$H$_5$ | 194° C. |
| 100 | CH$_2$CH$_2$ | CH$_2$CH$_2$ | O | Cl | H | 4-Cl-C$_6$H$_4$ | H | C$_2$H$_5$ | 199° C. |
| 101 | (R/S)—CHCH$_3$ | CH$_2$CH$_2$ | O | Cl | H | 3-OCH$_3$-C$_6$H$_4$ | H | C$_2$H$_5$ | 107° C. |

TABLE 7-continued

Examples of the compounds of the formula (I)

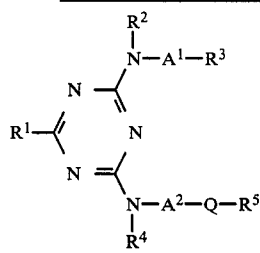

(I)

| Example No. | A¹ | A² | Q | R¹ | R² | R³ | R⁴ | R⁵ | Melting point or refractive index |
|---|---|---|---|---|---|---|---|---|---|
| 102 | (R/S)—CHCH₃ | CH₂CH₂ | O | Cl | H | ![p-Br-C₆H₄] | H | C₂H₅ | 47° C. |
| 103 | (R/S)—CHCH₃ | CH₂CH₂ | O | Cl | H | ![p-N(CH₃)₂-C₆H₄] | H | C₂H₅ | $n_D^{21}$ = 1.5721 |
| 104 | (R/S)—CHCH₃ | CH₂CH₂ | O | Cl | H | ![2,4,6-trimethylphenyl] | H | C₂H₅ | 125–127° C. |
| 105 | CH₂ | CH₂CH₂ | O | Cl | H | ![3,4-dichlorophenyl] | H | C₂H₅ | 182° C. |
| 106 | CH₂CH₂ | CH₂CH₂ | O | Cl | H | ![3,4-dimethoxyphenyl] | H | OCH₃ | 170° C. |
| 107 | CH₂CH₂ | CH₂CH₂ | O | Cl | H | ![2-chlorophenyl] | H | C₂H₅ | 190° C. |
| 108 | CH₂CH₂ | CH₂CH₂ | O | Cl | H | ![3-methoxyphenyl] | H | C₂H₅ | 175° C. |
| 109 | CH₂CH₂ | CH₂CH₂ | O | OCH₃ | H | ![4-methylphenyl] | H | C₂H₅ | 245° C. |
| 110 | (R/S)—CHCH₃ | —(CH₂)₃— | O | OCH₃ | H | ![4-bromophenyl] | H | CH₃ | $n_D^{21}$ = 1.5830 |

TABLE 7-continued

Examples of the compounds of the formula (I)

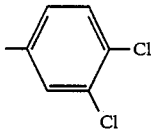

| Example No. | $A^1$ | $A^2$ | Q | $R^1$ | $R^2$ | $R^3$ | $R^4$ | $R^5$ | Melting point or refractive index |
|---|---|---|---|---|---|---|---|---|---|
| 111 | (R/S)—CHCH$_3$ | CH$_2$CH$_2$ | O | OCH$_3$ | H | 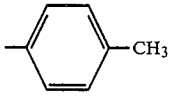 | H | C$_2$H$_5$ | $n_D^{21} = 1.5762$ |
| 112 | (R/S)—CHCH$_3$ | CH$_2$CH$_2$ | O | OCH$_3$ | H | 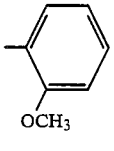 | H | C$_2$H$_5$ | $n_D^{21} = 1.5560$ |
| 113 | (R/S)—CHCH$_3$ | —(CH$_2$)$_3$— | O | OCH$_3$ | H | 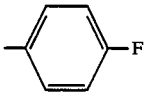 | H | CH$_3$ | $n_D^{21} = 1.5638$ |
| 114 | CH$_2$CH$_2$ | —(CH$_2$)$_3$— | O | OCH$_3$ | H | 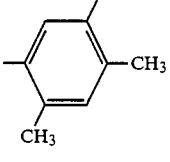 | H | CH$_3$ | 95–96° C. |
| 115 | (R/S)—CHCH$_3$ | —(CH$_2$)$_3$— | O | OCH$_3$ | H | 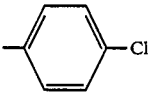 | H | CH$_3$ | 76° C. |
| 116 | (R/S)—CHCH$_3$ | CH$_2$CH$_2$ | O | OCH$_3$ | H | 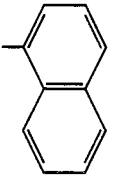 | H | C$_2$H$_5$ | 250° C. |
| 117 | (R/S)—CHCH$_3$ | —(CH$_2$)$_3$— | O | Cl | H | 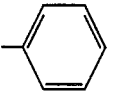 | H | CH$_3$ | 88° C. |
| 118 | C(CH$_3$)$_2$ | —(CH$_2$)$_3$— | O | Cl | H | | H | CH$_3$ | 138° C. |

EXAMPLE 119

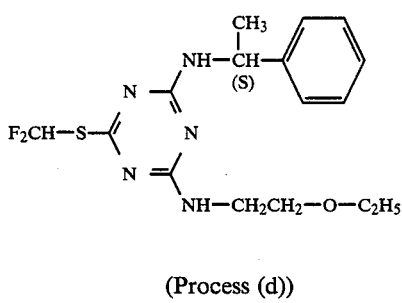

(Process (d))

A mixture of 8.0 g (0.025 mol) of (S)-2-mercapto-4-(2-ethoxy-ethylamino)-6-(1-phenyl-ethylamino)-s-triazine, 4.0 g (0.10 mol) of sodium hydroxide, 6 ml of water and 17 ml of isopropanol is heated at 56° C. for 30 minutes and then cooled to 20° C. Chlorodifluoromethane is then introduced into this mixture for 3 hours. The mixture is then diluted with 200 ml of water and shaken with methylene chloride, and the organic phase is separated off, washed with water, dried with sodium sulphate and filtered. The solvent is carefully distilled off from the filtrate in a waterpump vacuum.

6.1 g (66% of theory) of (S)-2-difluoromethylthio-4-(2ethoxy-ethylamino)-6-(1-phenyl-ethylamino)-s-triazine are obtained as an oily residue of refractive index $n_D25 = 1.5518$.

EXAMPLE 120

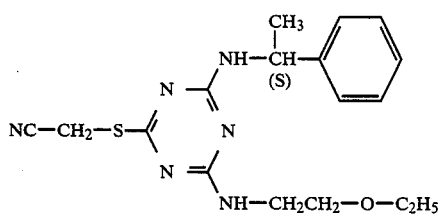

(Process (d))

A mixture of 8.0 g (0.025 mol) of (S)-2-mercapto-4-(2-ethoxy-ethylamino)-6-(1-phenyl-ethylamino)-s-triazine, 4.0 g (0.10 mol) of sodium hydroxide, 6 ml of water and 17 ml of isopropanol is heated at 56° C. for 30 minutes and then cooled to 20° C. After addition of 3.0 g (0.025 mol) of bromoacetonitrile, the reaction mixture is stirred at 20° C. for 4 hours and then worked up as described in Example 119.

5.2 g (56% of theory) of (S)-2-cyanomethylthio-4-(2-ethoxy-ethylamino)-6-(1-phenyl-ethylamino)-s-triazine are obtained as an oily residue.

STARTING SUBSTANCES OF THE FORMULA (II)

EXAMPLE (II-1)

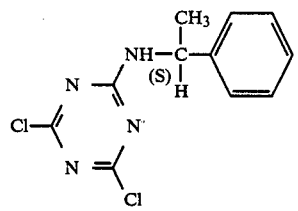

A solution of 24.2 g (0.2 mol) of (S)-1-phenyl-ethylamine in 50 ml of tetrahydrofuran is added dropwise to a solution, cooled to −30° C. to −40° C., of 18.4 g (0.1 mol) of 2,4,6-trichloro-s-triazine (cyanuric chloride) in 100 ml of tetrahydrofuran, with stirring. The reaction mixture is stirred at −30° C. to −40° C. for a further 45 minutes and then filtered cold with suction. The solvent is carefully distilled off from the filtrate under a waterpump vacuum. The oily residue which remains crystallizes after standing for a prolonged period of time.

25 g (93% of theory) of (S)-2,4-dichloro-6-(1-phenyl-ehtylamino)-s-triazine of melting point 75° C. are obtained.

The compounds of the formula (II) listed in Table 1 can be prepared analogously to Example (II-1).

STARTING SUBSTANCES OF THE FORMULA (IV)

EXAMPLE (IV-1)

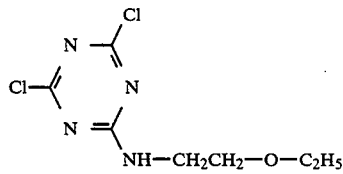

A solution of 9.7 g (0.11 mol) of 2-ethoxy-ethylamine and 11.0 g (0.11 mol) of triethylamine in 100 ml of tetrahydrofuran is added dropwise to a solution, cooled to −30° C. to −40° C., of 20 g (0.11 mol) of 2,4,6-trichloro-s-triazine (cyanuric chloride) in 100 ml of tetrahydrofuran, with stirring. The reaction mixture is stirred at −30° C. to −40° C. for 60 minutes and filtered with suction. The solvent is distilled off carefully from the filtrate under a waterpump vacuum. The residue which remains crystallizes after standing for a prolonged period of time.

21.2 g (84% of theory) of 2,4-dichloro-6-(2-ethoxy-ethylamino)-s-triazine of melting point 77° C. are obtained.

The compounds of the formula (IV) listed in Table 3 can be prepared analogously to Example (IV-1).

STARTING SUBSTANCES OF THE FORMULA (VII)

EXAMPLE (VII-1)

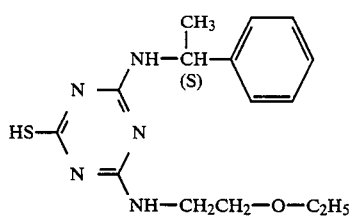

A mixture of 32.1 g (0.10 mol) of (S)-2-chloro-4-(2-ethoxy-ethylamino)-6-(1-phenyl-ethylamino)-s-triazine, 8.0 g (0.105 mol) of thiourea and 50 ml of dioxane is heated to boiling under reflux, cooled to about 80° C. after 1 to 2 minutes and, after the addition of 150 g of 2N sodium hydroxide solution, heated at 100° C. for a further 1 hour. After cooling, the mixture is filtered, the filtrate is neutralized with ammonium chloride, the precipitated crystalline product is isolated by filtration with suction, washed with water and dissolved in chloroform, and the solution is dried with magnesium sulphate and filtered. The solvent is carefully distilled off from the filtrate under a waterpump vacuum.

29.4 g (92% of theory) of (S)-2-mercapto-4-(2-ethoxy-ethylamino)-6-(1-phenyl-ethylamino)-s-triazine are obtained as a crystalline residue of melting point 53° C.

The compounds of the formula (VII) listed in Table 6 can be prepared analogously to Example (VII-1).

USE EXAMPLE

The compound of the following formula is employed as the comparison substance in the use example below:

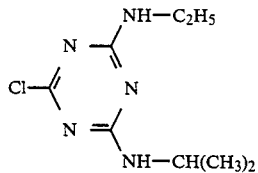

2-chloro-4-ethylamine-6-isopropylamino-s-triazine (atrazine).

EXAMPLE A

POST-EMERGENCE TEST

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction.

In this test, for example, the compounds according to Preparation Examples (1) or (2) and (3) exhibit better selectivity and a substantially stronger action than the comparison substance (A).

It will be understood that the specification and examples are illustrative but not limitative of the present invention and that other embodiments within the spirit and scope of the invention will suggest themselves to those skilled in the art.

We claim:

1. A substituted triazine of the formula

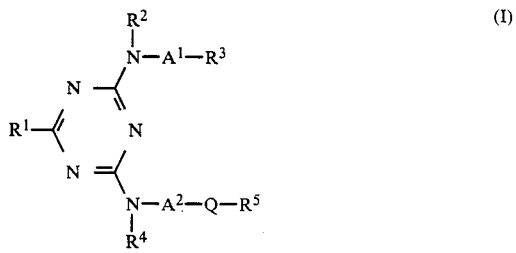

in which
$A^1$ represents optionally branched and optionally phenyl-substituted alkanediyl with 1 to 4 carbon atoms,
$A^2$ represents optionally branched alkanediyl with 1 to 4 carbon atoms,
Q represents oxygen, sulphur, NH or N-($C_1$-$C_4$-alkyl),
$R^1$ represents hydrogen, hydroxyl, nitro, cyano, cyanoamino, azido, fluorine, chlorine, bromine, iodine, $C_1$-$C_4$-alkoxy, $C_1$-$C_4$-alkylthio (which is optionally substituted by cyano, fluorine and/or chlorine), $C_1$-$C_4$-alkyl, $C_1$-$C_4$-alkoxy-carbonyl, aminocarbonyl, $C_1$-$C_4$-alkyl-amino-carbonyl, di-($C_1$-$C_4$-alkyl)-amino-carbonyl, amino, $C_1$-$C_4$-alkylamino or di-($C_1$-$C_4$-alkyl)-amino,
$R^2$ represents hydrogen, $C_1$-$C_4$-alkyl, $C_2$-$C_4$-alkenyl or $C_2$-$C_4$-alkinyl,
$R^3$ represents an aromatic or heteroaromatic radical from the group consisting of phenyl, naphthyl, pyridyl, quinolinyl, isoquinolinyl, pyrimidinyl, furyl, thienyl, pyrrolyl, pyrazolyl and imidazolyl which is optionally substituted by fluorine, chlorine, bromine, iodine, cyano, nitro, $C_1$-$C_4$-alkyl (which is optionally substituted by fluorine and/or chlorine), $C_1$-$C_4$-alkoxy or $C_1$-$C_2$-alkylenedioxy (which are optionally substituted by fluorine and/or chlorine), $C_1$-$C_4$-alkylthio, $C_1$-$C_4$-alkyl-sulphinyl or $C_1$-$C_4$-alkylsulphonyl (which are optionally substituted by fluorine and/or chlorine), di-($C_1$-$C_2$-alkyl)-amino and/or by $C_1$-$C_4$-alkoxy-carbonyl,
$R^4$ represents hydrogen, $C_1$-$C_4$-alkyl, $C_2$-$C_4$-alkenyl or $C_2$-$C_4$-alkinyl and
$R^5$ represents hydrogen or $C_1$-$C_4$-alklyl.

2. A compound according to claim 1, in which
$A^1$ represents optionally branched and optionally phenyl-substituted alkanediyl with 1 to 3 carbon atoms, A² represents optionally branched alkanediyl with 1 to 3 carbon atoms, Q represents oxygen, sulphur, NH or N—CH₃, R¹ represents cyanoamino, azido, fluorine, chlorine, bromine, methoxy, ethoxy, methylthio, ethylthio, difluoromethylthio, cyanomethylthio, methyl, amino, methylamino or dimethylamino, R² represents hydrogen or methyl, R³ represents phenyl or naphthyl which are optionally substituted by fluorine, chlorine, bromine, cyano, nitro, methyl, ethyl, methoxy, and/or ethoxy, or represents pyridyl which is optionally substituted by fluorine, chlorine, bromine, cyano, nitro, methyl, ethyl, methoxy and/or ethoxy, or represents furyl which is optionally substituted by fluorine, chlorine, bromine, methyl and/or ethyl, R⁴ represents hydrogen or methyl and R⁵ represents $C_1-C_3$-alkyl.

3. A compound according to claim 1, wherein such compound is (S)-2-chloro-4-(2-ethoxy-ethylamino)-6-(1-phenyl-ethylamino)-s-triazine of the formula

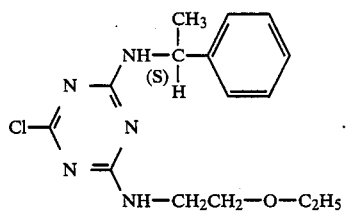

4. A compound according to claim 1, wherein such compound is (S)-2-methoxy-4-(2-ethoxy-ethylamino)-6-(1-phenyl-ethylamino)-s-triazine of the formula

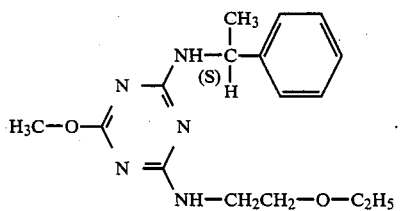

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is (S)-2-chloro-4-(2-ethoxy-ethylamino)-6-(1-phenyl-ethylamino)-s-triazine or (S)-2-methoxy-4-(2-ethoxy-ethylamino)-6-(1-phenyl-ethylamino)-s-triazine.

8. A mercaptotriazine of the formula

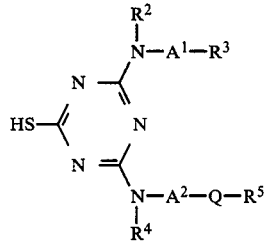

in which

A¹ represents optionally branched and optionally phenyl-substituted alkanediyl with 1 to 4 carbon atoms, A² represents optionally branched alkanediyl with 1 to 4 carbon atoms, Q represents oxygen, sulphur, NH or N-($C_1-C_4$-alkyl), R² represents hydrogen, $C_1-C_4$-alkyl, $C_2-C_4$-alkenyl or $C_2-C_4$-alkinyl, R³ represents an aromatic or heteroaromatic radical from the group consisting of phenyl, naphthyl, pyridyl, quinolinyl, isoquinolinyl, pyrimidinyl, furyl, thienyl, pyrrolyl, pyrazolyl and imidazolyl which is optionally substituted by fluorine, chlorine, bromine, iodine, cyano, nitro, $C_1-C_4$-alkyl (which is optionally substituted by fluorine and/or chlorine), $C_1-C_4$-alkoxy or $C_1-C_2$-alkylenedioxy (which are optionally substituted by fluorine and/or chlorine), $C_1-C_4$-alkylthio, $C_1-C_4$-alkyl-sulphinyl or $C_1-C_4$-alkylsulphonyl (which are optionally substituted by fluorine and/or chlorine), di-($C_1-C_2$-alkyl)-amino and/or by $C_1-C_4$-alkoxy-carbonyl, R⁴ represents hydrogen, $C_1-C_4$-alkyl, $C_2-C_4$-alkenyl or $C_2-C_4$-alkinyl and R⁵ represents hydrogen or $C_1-C_4$-alkyl.

* * * * *